US006652509B1

(12) United States Patent
Helgren et al.

(10) Patent No.: US 6,652,509 B1
(45) Date of Patent: Nov. 25, 2003

(54) HOUSING CAPABLE OF CONNECTING A CONTAINER TO A MEDICAL DEVICE

(75) Inventors: R. Hayes Helgren, Mundelein, IL (US); Kenneth A. Hsu, Highland Park, IL (US); Gary L. Johnston, Libertyville, IL (US); Ray A. Winfield, Bristol, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/541,261

(22) Filed: Apr. 3, 2000

(51) Int. Cl.[7] ........................ A61M 25/16; A61M 25/18

(52) U.S. Cl. ........................................ 604/535; 604/905

(58) Field of Search ................................ 604/533, 534, 604/535, 536, 905

(56) References Cited

U.S. PATENT DOCUMENTS 3,330,282 A 7/1967 Visser et al.
3,592,245 A 7/1971 Schneller et al.
3,977,555 A * 8/1976 Larson ....................... 206/363
4,360,024 A 11/1982 Wallace
4,439,188 A 3/1984 Dennehey et al.
4,511,163 A 4/1985 Harris et al.
4,643,309 A 2/1987 Evers
4,877,065 A 10/1989 Lamboy et al.
5,024,256 A * 6/1991 Vadher ........................ 140/27
5,312,377 A 5/1994 Dalton
5,338,314 A 8/1994 Ryan
5,409,125 A 4/1995 Kimber et al.
5,501,426 A 3/1996 Atkinson et al.
5,505,235 A 4/1996 Gorokhovsky et al.
5,514,117 A 5/1996 Lynn
5,549,583 A 8/1996 Sanford et al.
5,603,706 A 2/1997 Wyatt et al.
5,803,284 A 9/1998 Grimard
5,836,923 A * 11/1998 Mayer ........................ 604/246
5,871,110 A * 2/1999 Grimard et al. ............ 215/249
5,891,129 A 4/1999 Daubert et al.
5,902,298 A 5/1999 Niedospial, Jr. et al.
5,954,104 A 9/1999 Daubert et al.
5,964,260 A 10/1999 Chudy
6,070,623 A * 6/2000 Aneas ......................... 141/27
6,258,078 B1 * 7/2001 Thilly ........................ 206/363

FOREIGN PATENT DOCUMENTS

EP 0593224 4/1994
WO 9837853 9/1998

* cited by examiner

*Primary Examiner*—Brain L. Casler
*Assistant Examiner*—Mark K. Han
(74) *Attorney, Agent, or Firm*—David L. Weinstein

(57) ABSTRACT

A housing that can be used to form and maintain a fluid-tight connection between a container and a medical device. The housing comprises an internal receiving surface circumscribing a cavity into which a fitting of the medical device can be inserted. The internal receiving surface comprises a first wall portion having a first contact annulus and a second wall portion having a second contact annulus. Upon insertion of the fitting into an opening in the cavity of the housing, the fitting forms a primary seal with the first contact annulus and a secondary seal with the second contact annulus. The primary seal is formed as the surface of the fitting contacts the first contact annulus of the internal receiving surface of the housing. The secondary seal is formed as the surface of the fitting contacts the second contact annulus of the internal receiving surface of the housing.

24 Claims, 7 Drawing Sheets

HOUSING CAPABLE OF CONNECTING A CONTAINER TO A MEDICAL DEVICE

BACKGROUND OF THE INVENTION

1. Field of the Invention

The invention relates to a housing that is capable of connecting a container and a medical device. The medical device can comprise, for example, a syringe, an infusion set, or the like. The container can comprise a bag, a vial, a tube, or other container.

2. Discussion of the Art

Many pharmaceutical products are delivered to pharmacies in sealed containers such as glass or plastic vials, glass or plastic bottles, and flexible bags. Such containers can contain a powdered or lyophilized formulation of a pharmaceutical product that must be reconstituted with an aqueous diluent prior to administration to a patient. In addition, such containers can contain a solution or suspension formulation of a pharmaceutical product that can be withdrawn from the container and administered directly to a patient, for example, by parenteral administration.

Most pharmaceutical vials are sealed by a pierceable stopper that is press-fit into the mouth of a vial to thereby isolate the contents of the vial from the external environment of the vial. In order to access the pharmaceutical product within the vial, it is necessary either to pierce the stopper or remove the stopper from the vial. A conventional syringe can be used to add a diluent to the vial and/or to withdraw liquid from the vial. The syringe has a hollow needle that is pushed through the stopper and into communication with the contents of the vial. The plunger of the syringe can be depressed to dispense a diluent into the vial or pulled outwardly to draw liquid from the vial into the syringe.

The piercing of stoppers of vials typically has been achieved through the use of sharp, small-bored needles. Standard hypodermic syringe needles are particularly useful for this purpose because they allow the pharmaceutical product to be aseptically withdrawn from the vial and parenterally administered to a patient using a single device, thereby minimizing risk of contamination of the pharmaceutical product. In this mode, needles are typically connected to the syringe by means of a Luer-lock fitting. Luer-lock fittings are known to those skilled in the art. Such a fitting has been used in medical applications for joining an injection needle to a syringe, to link catheters, to link infusion sets, and to provide fluid communication for aqueous solutions of medicaments in a variety of settings. Typically, the Luer-lock fitting has a taper that matches the taper of the interior wall portion of the opening of the device into which it is inserted. Force is used to introduce the Luer-lock fitting into the opening of the device, and the matched tapers provide a substantially leak-proof seal.

The tapered structure of the Luer-lock fitting is subject to well-known and understood mechanical standards. Luer-lock fittings can be made of glass or metal, but are typically made of thermoplastic materials, such as, for example, polycarbonate, polypropylene, polystyrene, polyvinyl chloride, and the like. The experience of the industry has been that the Luer-lock fitting has great value, but is not free of operating problems. Conventionally, Luer-lock fittings are made from rigid thermoplastic materials, which provide little flexibility in the seal region and limit the depth that the male member of the Luer-lock fitting can be inserted into the receiving member of the Luer-lock fitting.

Examples of conventional tapered fittings are shown in Dennehey et al., U.S. Pat. No. 4,439,188 and Dalton, U.S. Pat. No. 5,312,377. The surfaces of the tapered male member of the fitting and the tapered female member of the fitting have a matched taper in these fittings. In these conventional designs, it is required that the taper of the mating surfaces of the tapered male member of the fitting and the tapered female member of the fitting be closely matched and come in close contact to make a satisfactory seal. Slight errors in the manufacturing of these tapered members typically result in a seal that either cannot be initially achieved or subsequently maintained.

Any moment of force normal to the line of contact of the male member of the fitting and the female member of the fitting can result in failure of the seal. There is a need for a device that can compensate for Luer-lock fittings that deviate dimensionally from current industry standards, yet still provide a satisfactory seal. There is also a need to reduce the amount of force or effort required by the user to insert the male member of a Luer-lock fitting into the opening of the female member of the Luer-lock fitting. It is also desired that the seal effected between the male member of the Luer-lock fitting and the female member of the Luer-lock fitting provide a positive sense of engagement, or "feel" to the user, in order to confirm that the male member of the Luer-lock fitting and the female member of the Luer-lock fitting are fully engaged, i. e., that the seal has been formed in such a manner that it will survive expected use and remain engaged even when subjected to a moment of force normal to the line of contact of the male member of the Luer-lock fitting and the female member of the Luer-lock fitting.

SUMMARY OF THE INVENTION

In one aspect, this invention provides a housing that can be used to form and maintain a fluid-tight connection between a container and a medical device. The housing comprises an internal receiving surface circumscribing a cavity into which a fitting of the medical device can be inserted. The internal receiving surface comprises a first wall portion having a first contact annulus and a second wall portion having a second contact annulus. Upon insertion of the fitting into an opening in the cavity of the housing, the fitting forms a primary seal with the first contact annulus and a secondary seal with the second contact annulus. The primary seal is formed as the surface of the fitting contacts the first contact annulus of the internal receiving surface of the housing. A hoop stress caused by the contact between the fitting and the first contact annulus produces a strain in the wall portion of the housing adjacent to the first contact annulus. This strain allows the diameter of the first contact annulus to expand. As the fitting continues to advance in the cavity, the first contact annulus eventually expands to a sufficient diameter to allow the fitting to contact the second contact annulus. The secondary seal is formed as the surface of the fitting contacts the second contact annulus of the internal receiving surface of the housing.

The housing uses a relatively flexible receiving surface in conjunction with a relatively rigid fitting of a medical device to form a reliable fluid-tight connection. Neither the interior of the housing nor the fitting require either precisely matched tapered surfaces or precise machining. The housing provides retention of the medical device by providing frictional contact between the first contact annulus of the internal receiving surface of the housing and the fitting and frictional contact between the second contact annulus of the internal receiving surface of the housing and the fitting. The application of only a relatively low force is needed to form the primary and the secondary seals, and the seals thus formed will provide to the user a positive sense of engagement that indicates to the user that a durable, fluid-tight connection has been formed.

In another aspect, the housing of the invention can be used to establish a fluid-tight connection between a fitting, e.g., a Luer-lock fitting, of a medical device, e.g., a syringe, and a stopper disposed in a container, e.g., a vial. The connection results from the interaction between the fitting and the housing, which is disposed over the stopper in the container. The housing has an internal receiving surface surrounding a cavity into which the fitting is inserted. The internal receiving surface of the housing comprises a first wall portion having a first contact annulus and a second wall portion having a second contact annulus, which annuli provide two seals, a primary seal at the first contact annulus and a secondary seal at the second contact annulus. The seals are formed in the same manner as described previously. The housing can be used in conjunction with a penetrator device that is disposed within the cavity of the housing, which is disposed over the stopper. As the fitting is introduced into the opening in the cavity of the housing, the fitting can cause the penetrator device to move towards the stopper and pierce the stopper by means of a pointed end on the penetrator device, thereby forming an opening in the stopper. Once the stopper is penetrated, then fluid can be withdrawn from the container by means of the medical device, such as, for example, a syringe.

The housing of this invention provides a reliable fluid-tight connection between a container and a medical device. The fluid-tight connection results from the primary seal that is formed by the contact between the exterior surface of the fitting and the first contact annulus of the internal receiving surface of the housing and the secondary seal that is formed by the contact between the exterior surface of the fitting and the second contact annulus of the internal receiving surface of the housing. As a result of the force generated in placing the fitting into the housing, the primary and secondary seals are formed quickly, creating a reliable seal with minimal insertion force.

The fitting can be inserted into the cavity of the housing with relatively low force to provide high frictional retention forces. Such an insertion preferably requires less than a full turn of the fitting to provide a satisfactory fluid-tight seal.

The invention facilitates rapid and safe access to the contents stored within a sealed container. The invention is especially suitable for use with a container such as a glass or plastic vial containing a pharmaceutical product or medicament. However, it will be appreciated that other applications of the present invention are feasible, including, but not limited, applications in connection with parenteral tube sets. The pharmaceutical product may be in liquid form, e.g., a solution or suspension of the product, or in a solid form, e.g., a powdered or lyophilized form of the product. The invention is especially useful with a conventional vial, which is normally sealed with a rubber stopper, which, in turn, is to be pierced by the hollow needle of a hypodermic syringe. When the stopper is pierced, the contents of the vial can be diluted or reconstituted with the contents of the syringe. Alternatively, the contents of the vial can be withdrawn into the syringe for subsequent discharge into another container system or for administration to a patient.

Numerous other advantages and features of the present invention will become readily apparent from the following detailed description of the invention, from the claims, and from the accompanying drawings and legends.

BRIEF DESCRIPTION OF THE DRAWINGS

In the accompanying drawings, which form part of the specification, and in which like numerals are employed to designate like parts throughout the same.

DETAILED DESCRIPTION

Figure 1:
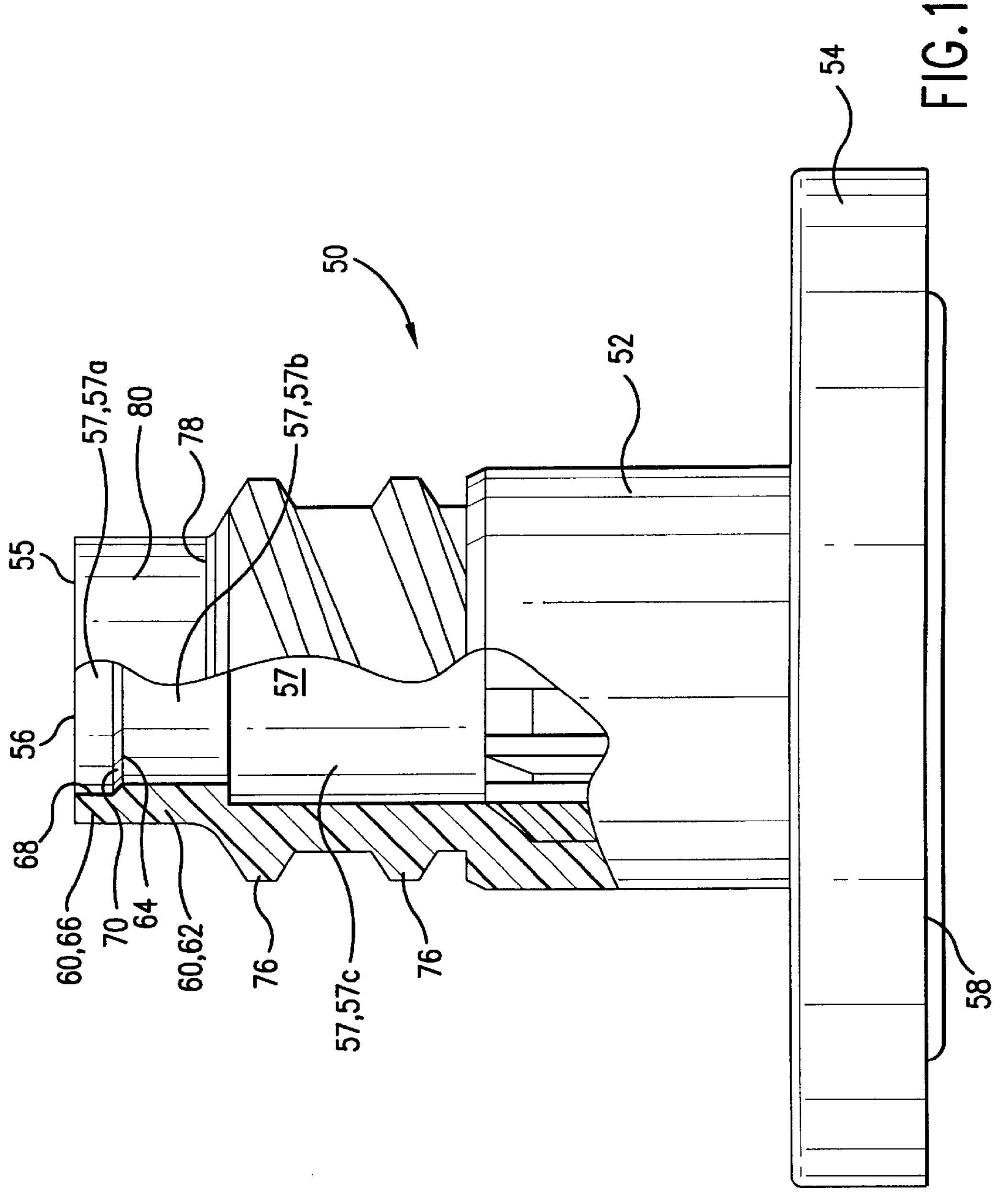
FIG. 1 is a side view in elevation, broken away, of a housing configured for use with a conventional glass or plastic vial.

While this invention is susceptible of embodiment in many different forms, this specification and the accompanying drawings disclose only some specific forms as examples of the invention. However, the invention is not intended to be limited to the embodiments so described. The scope of the invention is pointed out in the appended claims.

For ease of description, the components of this invention are described in the positions depicted in the accompanying drawings, and terms such as upper, lower, horizontal, etc., are used with reference to this position. It will be understood, however, that the components of this invention may be manufactured, stored, transported, used, and sold in an orientation other than the position described.

Figures illustrating the components show some mechanical elements that are known and that will be recognized by one skilled in the art. The detailed descriptions of such known elements are not necessary to an understanding of the invention, and accordingly, are herein presented only to the degree necessary to facilitate an understanding of the novel features of the invention.

This invention can be used with certain other conventional instruments and/or components, the details of which, although not fully illustrated or described, will be apparent to those having skill in the art and an understanding of the necessary functions of such components.

In one aspect, the invention provides a housing for establishing a fluid-tight connection between a fitting, such as, for example, a male Luer tapered fitting having an axial passageway, and a container, such as, for example, a vial of fluid. The housing of this invention is especially suitable for use with a syringe employing a Luer-lock fitting. However, it will be appreciated that other applications of the present invention are feasible including, but not limited to, applications involving parenteral tube sets. The invention is especially useful for providing a reliable connection with a fitting that may have dimensional variations. The reliable connection exhibits increased retention forces, thereby increasing the resistance to disconnection of the fitting from the housing.

As used herein, the term “housing” means an element that covers, protects, or supports. The term “wall” means an element serving to enclose an area. The term “shoulder” means a shoulderlike slope or projection. The expression "contact annulus" means a ringlike figure, part, structure, or marking of the housing that touches a fitting. The term "seal" means a fluidtight closure. The term "receiving surface" means a surface of an element that takes in or holds a different element. The term "diameter" means a straight line segment passing through the center of a figure, such as, for example, a circle, and terminating at the periphery. In this invention, the annulus is substantially circular in shape, however, on account of the difficulty encountered in forming annuli that are perfectly circular in shape, the annuli may not be perfectly circular in shape, in which case, the term "diameter" refers to a measured value that approximates the diameter of a circle.

Figure 2:
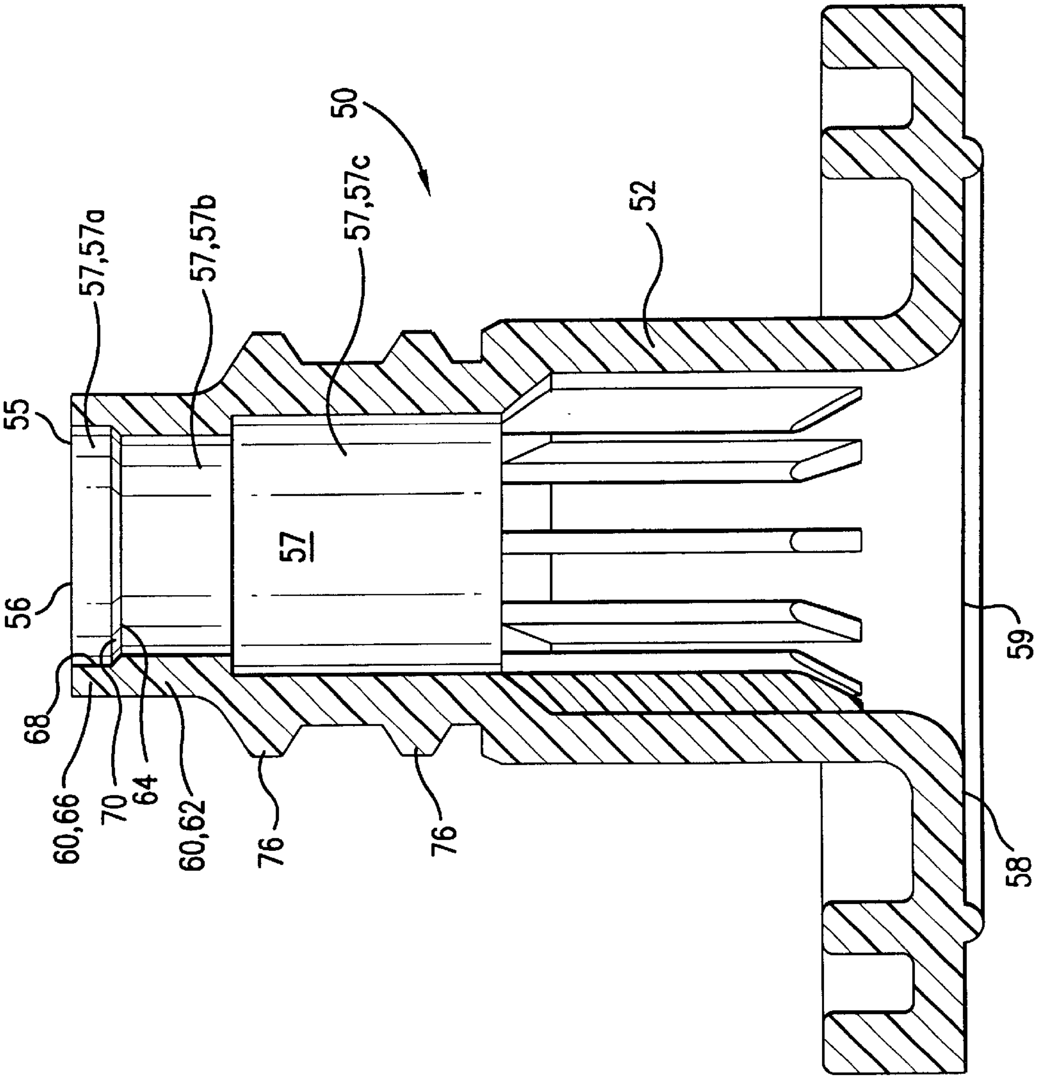
FIG. 2 is a cross-sectional view of the housing shown in FIG. 1.

FIGS. 1 and 2 illustrate a housing 50 configured for use with a conventional glass or plastic vial. However, it will be appreciated that the housing 50 can be adapted to a wide variety of containers and devices for storage of solids and fluids and transport of fluids. The depiction herein of the housing 50 is not intended to be limiting but instead represents one useful application of the present invention. For the purpose of this disclosure, all references to the terms "container" and "vial" are intended to include vials, bottles, flexible containers, parenteral or enteral tube sets, and equivalents thereof.

The housing 50 has a cylindrical neck 52 terminating in an annular flange 54, which facilitates attachment of the housing 50 to a container or vial. The housing 50 has an upper end 55 having an opening 56, which opens to an internal cavity 57, which extends through the housing 50. The cavity 57 comprises an upper cavity portion 57*a*, an intermediate cavity portion 57*b*, and a lower cavity portion 57*c*. The housing also has a lower end 58 having an opening 59, which opens to the internal cavity 57. The internal cavity 57 is surrounded by a wall 60, which comprises a first wall portion 62, which includes a first contact annulus 64, and a second wall portion 66, which includes a second contact annulus 68. The ratio of the thickness of the first wall portion 62 to the thickness of the second wall portion 66 is greater than unity, i. e., 1. The first contact annulus 64 has a diameter that is less than the diameter of the second contact annulus 68. The first contact annulus 64 has a diameter that is less than the diameter of the upper cavity portion 57*a*. Examples of dimensions of the housing range from a height of ½-inch to ¾-inch measured from the upper end 55 to the lower end 58 of the housing 50. An example of the diameter of the first contact annulus 64 is 0.166 inch. An example of the diameter of the second contact annulus 68 is 0.179 inch. An example of the thickness of the first wall portion 62 is 0.022 inch. The difference in annular diameter between the first contact annulus 64 and the second contact 68 preferably ranges from about 0.005 to about 0.02 inch. An annular shoulder 70 is located adjacent the first contact annulus 64.

Figure 3:
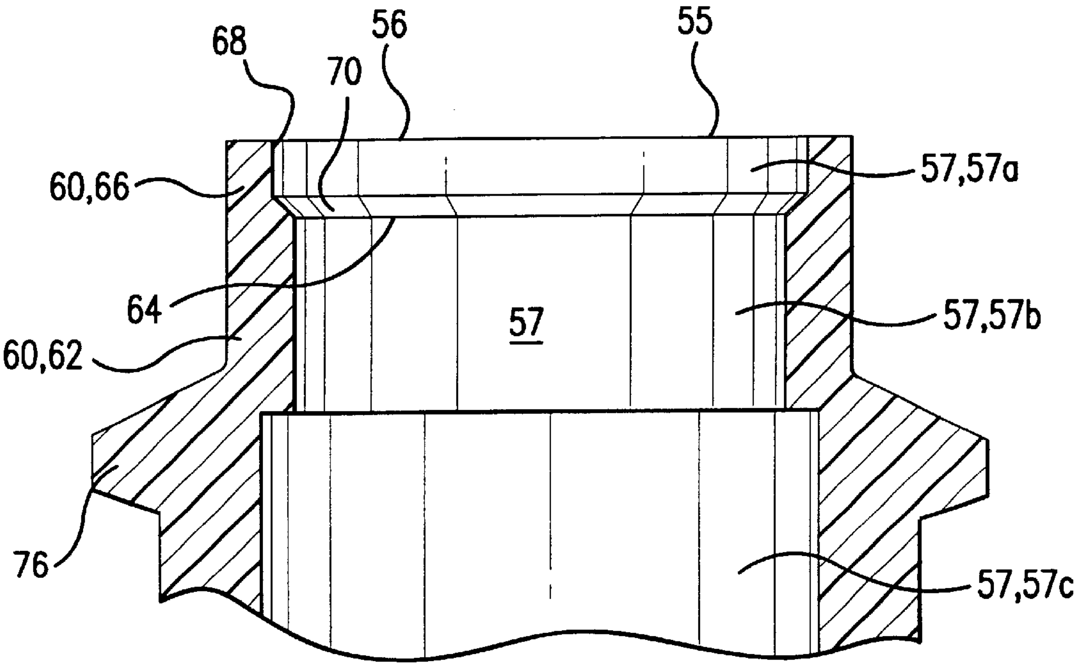
FIG. 3 is a partial cross-sectional view of the internal receiving surface of the housing shown in FIG. 1.
Figure 4:
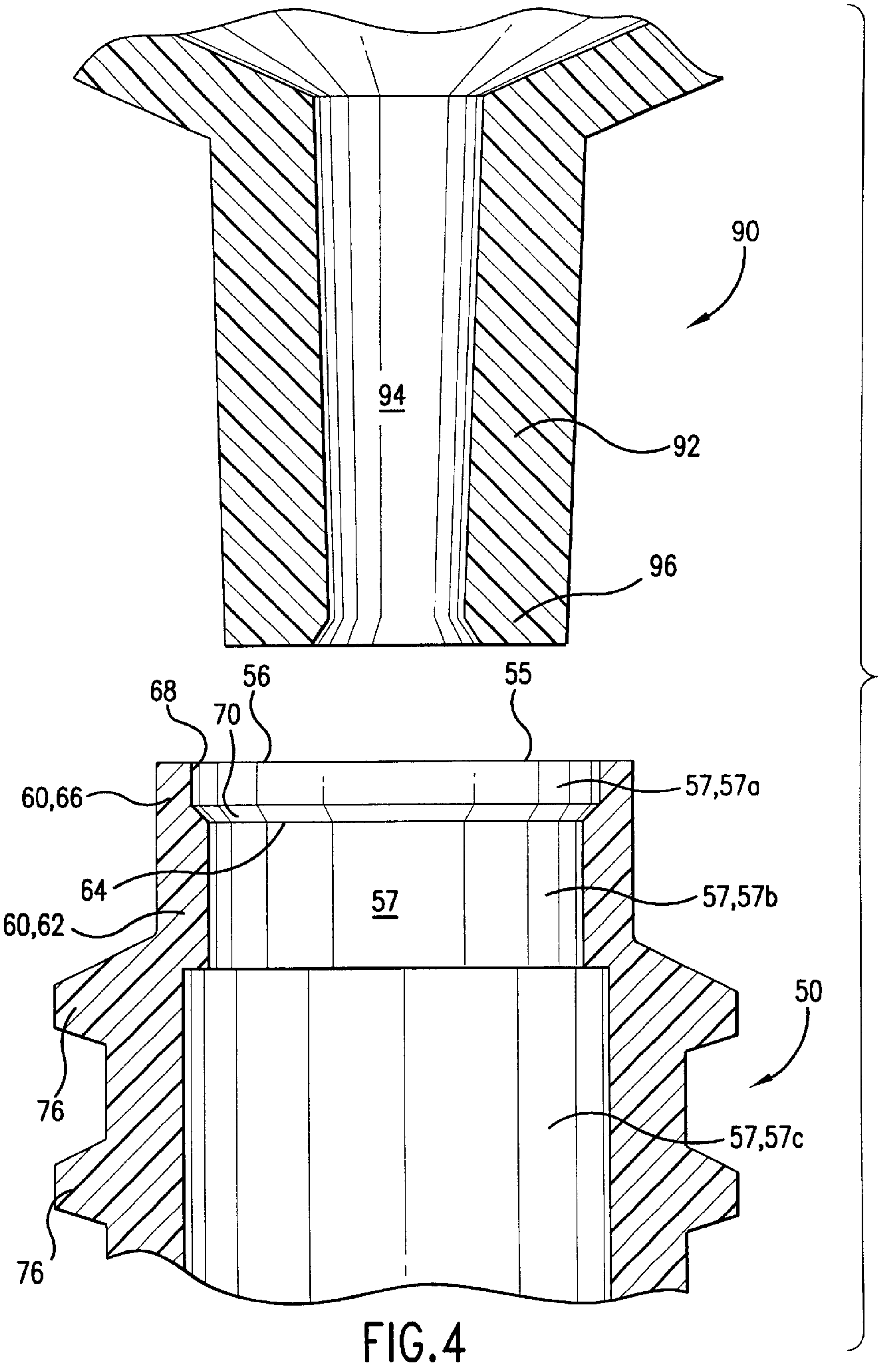
FIG. 4 is a partial cross-sectional view of a conventional Luer-lock fitting situated in a position preparatory to being inserted into the housing of this invention to form the primary and the secondary seals.
Figure 5:
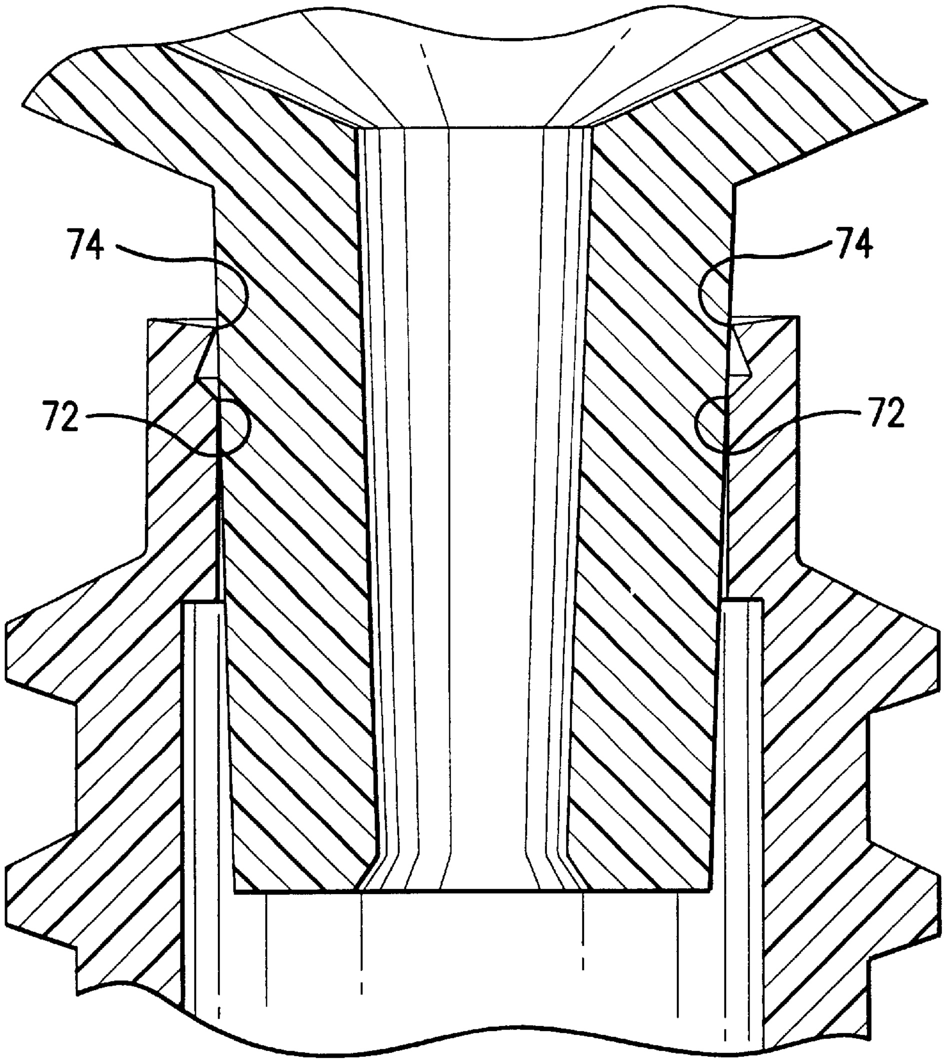
FIG. 5 is a cross-sectional view of the fitting of FIG. 4 inserted in the housing.

Referring now to FIGS. 3, 4, and 5, the wall portion 62 containing the first contact annulus 64 has a greater thickness than the wall portion 66 containing the second contact annulus 68. Thus, the first contact annulus 64 is associated with a relatively more rigid wall structure than is the second contact annulus 68. The wall portion 66 has relatively more flexibility than does the wall portion 62. The difference in flexibility in the wall portions in the embodiment shown is obtained by employing a wall portion 66 that is thinner than the wall portion 62. However, in alternative embodiments, the difference in flexibility can be obtained by providing a plurality of slots, preferably elongated, partially or completely through the wall portion 66. In this alternative embodiment, the wall portion 66 can be of equal thickness or of greater thickness than the wall portion 62. The distance between the first contact annulus 64 and the second contact annulus 68 must be sufficient so that at least two distinct seals, a primary seal 72 and a secondary seal 74, are formed. The primary seal 72 and the secondary seal 74 are shown in FIG. 5. The distance between the first contact annulus 64 and the second contact annulus 68 cannot be so great that the formation of at least two distinct seals is prohibited. An example of the nominal distance between the first contact annulus 64 and the second contact annulus 68 is 0.03 inch. As will be explained with respect to a Luer-lock fitting, these structural features provide an excellent fluid-tight connection and increased contact stress (higher force per unit area at the first and the second contact annuli), thereby increasing the resistance to disconnection between the Luer-lock fitting and the housing 50. Luer connectors, including Luer-lock fittings, are described in detail in U.S. Pat. No. 5,312,377, incorporated herein by reference.

Although only two contact annuli are shown in the embodiments of this invention, it is within the scope of this invention to add a third contact annulus, or even more contact annuli, to the housing 50. Each additional contact annulus, if employed, would result in an additional seal. Each additional seal would be placed at a higher level on the housing 50 than the previously numbered seal, e.g., the tertiary seal would be placed at a higher level than the secondary seal, and each additional seal would have the same relationship to the previously numbered seal that the secondary seal 74 has to the primary seal 72.

A portion of the housing 50 includes a laterally projecting formation 76, such as a conventional Luer-lock, double lead, helical thread, or the like. This laterally projecting formation 76 projects from the exterior surface 80 of the housing 50. The laterally projecting formation 76 is designed for engaging a mating thread system on an annular skirt of a medical device having a Luer connector, such as, for example, a syringe employing a Luer-lock fitting (as described in detail hereinafter). The laterally projecting formation 76 begins at a point 78 on the exterior surface 80 of the housing 50. It is preferred that the point 78 be placed at such a distance from the upper end 55 of the housing 50 that the axial length of the laterally projecting formation 76 is rendered sufficiently short that less than a full turn of the medical device is required to engage the Luer-lock fitting. It is preferred that the laterally projecting formation 76 extends along the exterior surface 80 of the housing 50 a distance sufficient to engage the Luer-lock fitting approximately one-half turn. However, it is within the scope of this invention that the laterally projecting formation 76 can be longer and can even extend to the upper end 55 of the housing 50.

Referring to FIG. 2, the lower cavity portion 57*c* communicates with the intermediate cavity portion 57*b*. The lower cavity portion 57*c* is open at the lower end 58 of the housing 50.

FIG. 4 shows a partial view in cross-section of a tip 90 of a medical device (not shown), such as, for example, a syringe, having a conventional Luer-lock fitting. The tip 90 has a wall 92 surrounding a bore 94, which is in communication with the body of the medical device (not shown). The exterior surface of the tip 90 is tapered, whereby the exterior diameter of the tip 90 is reduced to its minimum dimension at the distal end 96 of the tip 90. As used herein, the distal end 96 of the tip 90 is the end of the tip 90 that first enters the opening 56 of the housing 50. FIG. 4 illustrates the tip 90 in position to be inserted into the housing 50, a partial cross-sectional view of which is shown.

FIG. 5 shows the tip 90 fully inserted in the housing 50. Upon insertion of the tip 90 in the internal cavity 57 of the housing 50, the wall 92 of the tip 90 initially contacts the first contact annulus 64. A primary seal 72 is formed as the surface of the tip 90 contacts the first contact annulus 64. This contact causes a hoop stress to be exerted on the first contact annulus 64. This hoop stress creates a strain in the wall portion adjacent to the first contact annulus 64. This strain causes lateral expansion of the first contact annulus 64. As the tip 90 continues to advance in the cavity 57, the first contact annulus 64 eventually expands to a sufficient diameter to allow the tip 90 to contact the second contact annulus 68. The secondary seal is formed as the exterior surface of the tip 90 contacts the second contact annulus 68 of the housing 50. Contact of the tip 90 with the second contact annulus 68 is facilitated by the tapered shape of the tip 90.

When the tip 90 is fully inserted into the housing 50, a primary seal 72 is formed between the wall 92 of the tip 90 and the first contact annulus 64 and a secondary seal 74 is formed between the wall 92 of the tip 90 and the second contact annulus 68. After the primary seal 72 and the secondary seal 74 are established, the first contact annulus 64 and the second contact annulus 68 are displaced axially. If a lateral force sufficient to create a moment is exerted anywhere along the major axis of a medical device attached to the fitting held by the primary seal 72 and the secondary seal 74, the primary seal 72 and the secondary seal 74 will resist being broken by the force. Moreover, the primary seal 72 and the secondary seal 74 will resist the disengagement of the medical device from the housing.

Any thermoplastic material can be used in the manufacture of the housing 50 containing the contact annuli 64, 68. Conventional thermoplastic materials include homopolymers and copolymers containing olefinic monomer groups. Representative examples of such homopolymers and copolymers include, but are not limited to, polyethylene, polypropylene, copolymers comprising ethylene and propylene monomeric groups, copolymers containing ethylene and hexalene monomeric groups, ethylenediene copolymers, and other polyolefinic materials. Additionally, other engineering plastics, such as, for example, polyamides, such as nylon, polyvinyl chlorides, polycarbonates, etc., can be used. The materials used to form the components used in this invention are selected on the basis of structural properties, ease of manufacture, and cost. Preferred materials for this invention comprise homopolymers and copolymers containing olefinic monomeric groups.

The housing 50 is preferably molded as a unitary structure from a thermoplastic material, such as polypropylene, nylon, polyethylene, ethylenecopropylene copolymers, ethylenecohexylene copolymers, and polyvinyl chloride. Polypropylene is an especially preferred material.

The components of the invention can be manufactured using any thermoplastic manufacturing technique that will provide the desired result. The components are preferably made by injection molding of thermoplastic materials into precision molds under pressure using conventional techniques. The dimensions of the first contact annulus 64 and the second contact annulus 68 can reasonably be maintained using conventional thermoplastic injection molding techniques.

Figure 6:
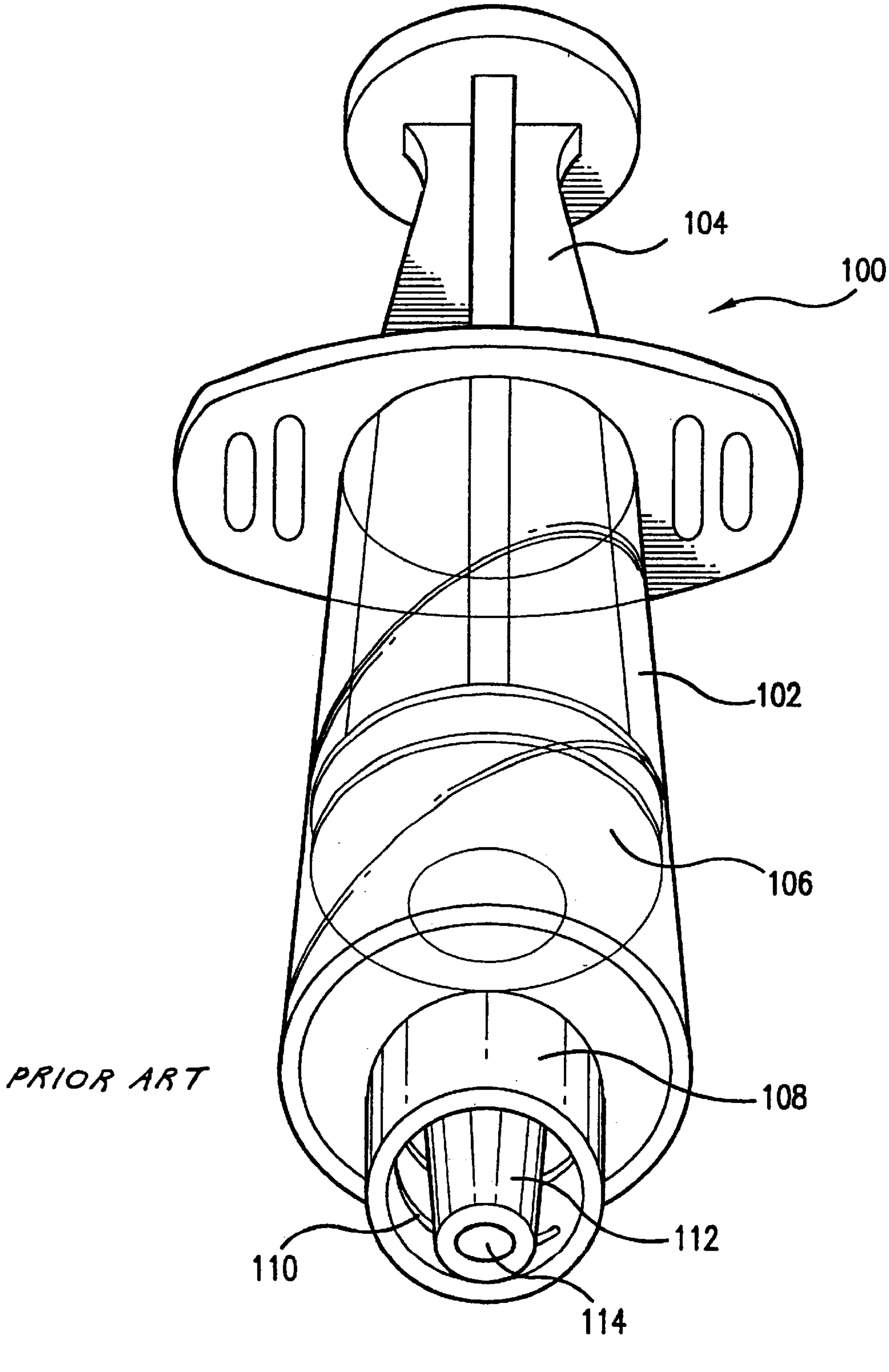
FIG. 6 is a perspective view of a conventional syringe employing a Luer-lock fitting.
Figure 7:
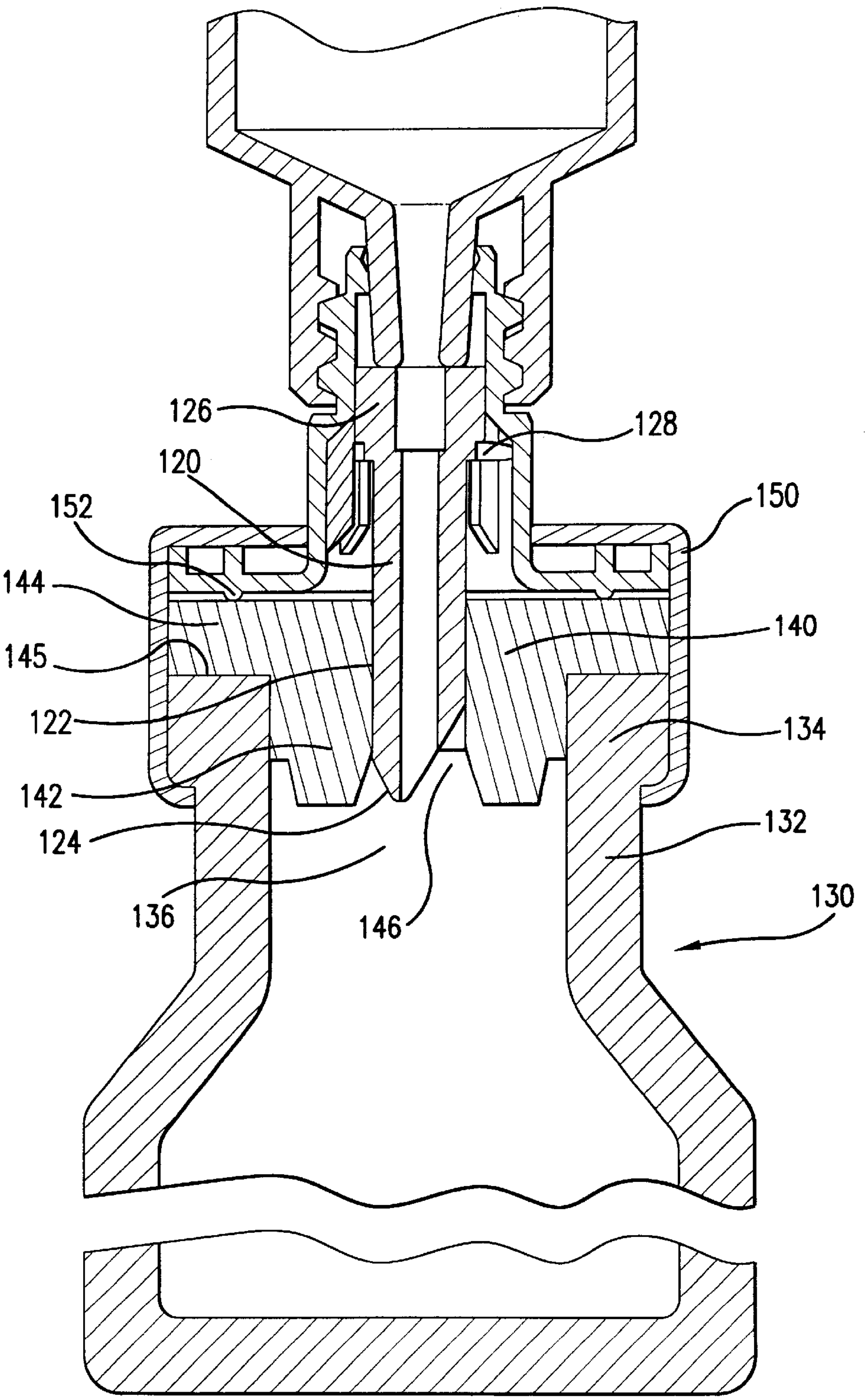
FIG. 7 is a cross-sectional view showing the syringe of FIG. 6 attached to the housing, with the housing installed on a vial. This view shows the penetrator device in the fully extended lowered position penetrating the stopper in the mouth of the vial.

FIGS. 6 and 7 illustrate the use of the housing of the present invention to couple a syringe 100 employing a Luer-lock fitting with a vial 130 containing a liquid. It will be appreciated that this description is for exemplary purposes only and that use of the present invention is not limited to a syringe employing a Luer-lock fitting or a vial containing a liquid.

The syringe 100 includes a barrel 102 and a telescopically received plunger 104. The distal end of the plunger 104 includes a piston 106 that engages with the interior cylindrical surface of the barrel 102 to form a seal between the piston 106 and the interior cylindrical surface of the barrel 102.

The distal end of the syringe 100 has an annular skirt 108, which is internally threaded with a conventional Luer-lock, double lead, helical thread system 110. A tip 112 projects from the, distal end of the barrel 102 within the annular skirt 108. The exterior surface of the tip 112 is tapered, whereby the exterior diameter of the tip 112 is reduced to its minimum dimension at the distal end of the tip 112. The tip 112 has formed therein a bore 114, which is in communication with the interior chamber 115 of the barrel 102, which chamber 115 is located below the piston 106.

As shown in FIG. 7, the syringe 100 can be coupled with the vial 130. The thread system 110 engages the thread system 76 of the housing 50. As relative rotation is effected between the syringe 100 and the vial 130, the tip 112 of the syringe 100 moves downwardly against the upper end of a penetrator device 120. This movement causes the penetrator device 120 to move downwardly through the internal cavity 57 of the housing 50.

The vial 130 has a cylindrical neck 132 terminating in an annular flange 134, which defines an opening 136 of the vial 130.

The mouth of the vial 130 contains a stopper 140. The stopper 140 is typically made from rubber or other suitable elastomeric material. The stopper 140 includes a central generally annular plug portion 142 and a head portion 144. The diameter of the head portion 144 is greater than the diameter of the plug portion 142. The head portion 144 functions as a supporting flange and is normally seated on the top end surface 145 of the flange 134 of the vial 130. The annular plug portion 142 of the stopper 140 defines an internal recess 146, which opens downwardly toward the contents of the vial 130. The stopper 140 prevents the removal of the contents of vial 130 unless and until the stopper 140 is either removed or penetrated. Typically, the annular plug portion 142 of the stopper 140 is received in the opening 136 of the vial 130 in a radially inwardly compressed condition and is retained within the opening 136 in the vial 130 by frictional engagement, which is established by the outward force of the annular plug portion 142 on the neck 132 of the vial 130.

The housing 50 is positioned on the head portion 144 of the stopper 140 and is held in place by ferrule 150, which retains the radially extending lower end of the housing 50. Ferrules are discussed in U.S. Ser. No. 09/282,959, filed Apr. 1, 1999, incorporated herein by reference. A ring 152 engages the head portion 144 of the stopper 140, thereby effecting a seal between the ring 152 and the head portion 144. A bottom peripheral portion of the ferrule 150 is crimped about the lower edge of the flange 134 of the vial 130.

A penetrator device 120 is disposed in the lower cavity portion **57*c* of the housing 50 and is axially aligned therein. The penetrator device 120 is capable of sliding in the lower cavity portion 57*c* of the housing 50. The penetrator device 120, which is adapted for being received in the housing 50, is a unitary structure made from plastic or metal material. The penetrator device 120 has a shank 122 having a point defining a pointed distal end 124. The penetrator device 120 has a hub 126 at the end of the shank 122 opposite the pointed distal end 124. The hub 126 defines the upper end of the penetrator device 120. The lower portion of the hub 126 includes an annular bead 128 having a diameter that establishes the diameter of the hub 126**.

The housing 50 and the penetrator device 120 are preferably constructed in such a manner that they are held together by frictional forces therebetween. The penetrator device 120 is initially positioned at an uppermost elevation (not shown) within the lower cavity portion 57*c* of the housing 50. The annular bead 128 disposed on the shank 122 of the penetrator device 120 establishes a slight interference fit with the interior surface of the lower cavity portion 57*c*. The lower cavity portion 57*c* may include longitudinal guide elements (not shown) for the penetrator device 120, such as the rib structure disclosed in U.S. Pat. No. 5,954,104 and incorporated herein by reference. The housing 50, with the penetrator device 120 inserted therein, is positioned with respect to the vial 130 in such a manner that the pointed distal end 124 of the penetrator device 120 is capable of piercing the internal recess 146 of the stopper 140 when the penetrator device 120 is actuated by coupling the Luer lock system 110 to the housing 50.

OPERATION

Operation of the present invention will now be described in conjunction with FIG. 7. It will be appreciated that this description is for exemplary purposes only and that the present invention is not limited to the example. As shown in FIG. 7, the syringe 100 is coupled with the housing 50. To this end, the syringe 100 is threadingly engaged with the thread system 76 on the housing 50. A relative rotation of approximately one-half turn is sufficient to effectively engage the syringe 100 and the vial 130. The tip 112 of the syringe 100 moves downwardly until it contacts the first contact annulus 64, thereby resulting in a hoop stress. The hoop stress resulting from this contact produces a strain in the wall portion of the housing adjacent to the first contact annulus 64. This strain allows the diameter of the first contact annulus 64 to expand. As the tip 112 of the syringe 100 continues to advance in the cavity, the first contact annulus 64 eventually expands to a sufficient diameter to allow the tip 112 of the syringe 100 to contact the second contact annulus 68. The secondary seal 74 is formed as the second contact annulus 68 of the housing 50 contacts the tip 112 of the syringe 100. Contact of the tip 112 with the second contact annulus 68 is facilitated by the tapered shape of the tip 112. See FIG. 7.

When the tip 112 of the syringe 100 is fully inserted in the housing 50, the primary seal 72 is formed by contact of the first contact annulus 64 with the exterior surface of the tip 112 of the syringe 100, and the secondary seal 74 is formed by contact of the second contact annulus 68 with the exterior surface of the tip 112 of the syringe 100.

Further, the tip 112 also engages the upper end of the penetrator device 120. This engagement pushes the penetrator device 120 downwardly along the lower cavity portion 57*c* of the housing 50. As the penetrator device 120 moves downwardly within the lower cavity portion 57*c* of the housing 50, the pointed distal end 124 of the penetrator device 120 pierces the stopper 140 and enters the internal recess 146 of the stopper 140, thereby establishing fluid communication between the vial 130 and syringe 100.

The housing of this invention can be used to form a fluid-tight seal between a container, such as a vial, and a medical device, such as a syringe, or other device capable of transferring fluids. The seal can be formed easily with minimal level of insertion force. The seal can be made without carefully aligning the container and the medical device.

The foregoing detailed description of the invention and the illustrations thereof demonstrate that numerous variations and modifications in apparatus and methods that embody the invention may be effected without departing from the true spirit and scope of the novel concepts or principles of this invention. The invention resides in the claims hereinafter appended.

What is claimed is:

1. A housing for establishing a fluid connection between a fitting and a medical device, said housing comprising an internal receiving surface circumscribing a cavity into which said fitting can be inserted, said internal receiving surface comprising a first wall portion having a first contact annulus and a second wall portion having a second contact annulus, wherein upon insertion of said fitting into said cavity of said housing, said fitting forms a primary seal with said first contact annulus and a secondary seal with said second contact annulus.

2. The housing of claim 1, wherein the distance between said first contact annulus and said second contact annulus is sufficient so that at least two distinct seals are formed.

3. The housing of claim 1, further including a laterally projecting formation for engaging a mating system on said medical device.

4. The housing of claim 3, wherein said laterally projecting formation extends for a distance sufficient to engage said mating system approximately one-half turn.

5. The housing of claim 1, wherein the ratio of the thickness of said first wall portion to the thickness of said second wall portion is greater than 1.

6. The housing of claim 1, wherein said first contact annulus has a diameter that is less than the diameter of said second contact annulus.

7. The housing of claim 1, wherein an annular shoulder is adjacent to said first contact annulus.

8. The housing of claim 1, wherein said fitting has a tapered shape.

9. An assembly comprising a medical device, a container, and a housing, said assembly comprising:

(a) a medical device having a fitting having a tapered exterior surface having a reduced diameter at a distal end and an axial passageway, (b) a container, and (c) a housing comprising an internal receiving surface circumscribing a cavity into which said fitting can be inserted, said internal receiving surface comprising a first wall portion having a first contact annulus and a second wall portion having a second contact annulus, wherein upon insertion of said fitting into said cavity of said housing, said fitting forms a primary seal with said first contact annulus and a secondary seal with said second contact annulus.

10. The assembly of claim 9, wherein the distance between said first contact annulus and said second contact annulus is sufficient so that at least two distinct seals are formed.

11. The assembly of claim 9, further including a laterally projecting formation for engaging a mating system on said medical device.

12. The assembly of claim 11, wherein said laterally projecting formation extends for a distance sufficient to engage said mating system approximately one-half turn.

13. The assembly of claim 9, wherein the ratio of the thickness of said first wall portion to the thickness of said second wall portion is greater than 1.

14. The assembly of claim 9, wherein said first contact annulus has a diameter that is less than the diameter of said second contact annulus.

15. The assembly of claim 9, wherein an annular shoulder is adjacent to said first contact annulus.

16. The assembly of claim 9, wherein said fitting has a tapered shape.

17. An assembly comprising a medical device, a container, and a housing, said assembly comprising:

(a) a medical device having a fitting having a tapered exterior surface having a reduced diameter at a distal end and an axial passageway, (b) a container comprising a mouth, which mouth is occluded by a stopper, and (c) a housing comprising an internal receiving surface circumscribing a cavity into which said fitting can be inserted, said internal receiving surface comprising a first wall portion having a first contact annulus and a second wall portion having a second contact annulus, wherein upon insertion of said fitting into said cavity of said housing, said fitting forms a primary seal with said first contact annulus and a secondary seal with said second contact annulus, wherein said housing further comprises a penetrator device disposed in said cavity of said housing, said penetrator device capable of sliding in said cavity of said housing, said penetrator device further capable of penetrating said stopper upon movement of said penetrator device within said cavity of said housing.

18. The assembly of claim 17, wherein the distance between said first contact annulus and said second contact annulus is sufficient so that at least two distinct seals are formed.

19. The assembly of claim 17, further including a laterally projecting formation for engaging a mating system on said medical device.

20. The assembly of claim 19, wherein said laterally projecting formation extends for a distance sufficient to engage said mating system approximately one-half turn.

21. The assembly of claim 17, wherein the ratio of the thickness of said first wall portion to the thickness of said second wall portion is greater than 1.

22. The assembly of claim 17, wherein said first contact annulus has a diameter that is less than the diameter of said second contact annulus.

23. The assembly of claim 17, wherein an annular shoulder is adjacent to said first contact annulus.

24. The assembly of claim 17, wherein said fitting has a tapered shape.

* * * * *